United States Patent [19]

Al-Samadi

[11] Patent Number: 5,635,071
[45] Date of Patent: Jun. 3, 1997

[54] RECOVERY OF CARBOXYLIC ACIDS FROM CHEMICAL PLANT EFFLUENTS

[75] Inventor: Riad A. Al-Samadi, Burlington, Canada

[73] Assignee: Zenon Airport Enviromental, Inc., Burlington, Canada

[21] Appl. No.: 375,789

[22] Filed: Jan. 20, 1995

[51] Int. Cl.⁶ .................................................. B01D 61/00
[52] U.S. Cl. ........................ 210/652; 210/651; 210/641; 210/653; 210/805
[58] Field of Search ..................... 210/652, 651, 210/653, 654, 641, 634, 805; 203/15, 16, 10, 14, 43, 48

[56] References Cited

U.S. PATENT DOCUMENTS

| | | | |
|---|---|---|---|
| 4,000,065 | 12/1976 | Ladha et al. | |
| 4,584,057 | 4/1986 | Rowe et al. | 510/652 |
| 4,655,928 | 4/1987 | Milton et al. | |
| 4,661,208 | 4/1987 | Homma et al. | 203/15 |
| 4,728,393 | 3/1988 | Peel | |
| 4,808,287 | 2/1989 | Hark | |
| 4,872,991 | 10/1989 | Bartels et al. | 210/654 |
| 4,904,389 | 2/1990 | Waldhoff et al. | 210/651 |
| 5,028,336 | 7/1991 | Bartels et al. | 210/651 |
| 5,104,492 | 4/1992 | King et al. | 203/15 |
| 5,145,584 | 9/1992 | Swamikannu | |
| 5,167,826 | 12/1992 | Eaton | |
| 5,248,427 | 9/1993 | Spiske et al. | 210/651 |
| 5,250,182 | 10/1993 | Bento et al. | 210/651 |
| 5,399,751 | 3/1995 | Gentry et al. | 203/16 |
| 5,492,625 | 2/1996 | Wytcherley et al. | 210/634 |

FOREIGN PATENT DOCUMENTS

| 91799 | 6/1982 | Japan | 210/652 |
|---|---|---|---|

*Primary Examiner*—Ana Fortuna
*Attorney, Agent, or Firm*—Andrew Alexander

[57] ABSTRACT

Provided is a method of removing carboxylic acids from effluent streams comprising the steps of pretreatment which may include chemical conditioning, clarification and filtering the effluent stream to remove suspended solid particles to provide a filtered stream. The filtered stream is subjected to membrane filtration to remove organic compounds having a molecular weight of greater than 150 while simultaneously permitting permeation of the membrane by the carboxylic acids to provide a membrane filtered stream. A reverse osmosis membrane is provided having a high pressure side and a low pressure side, and the membrane filtered stream is introduced to the high pressure side of the reverse osmosis membrane. The carboxylic acids are concentrated in the high pressure side of the reverse osmosis membrane. In a preferred embodiment, purified liquid (permeate) is neutralized and passed to the high pressure side of a second pass reverse osmosis membrane, producing a high-purity final permeate for plant reuse or discharge to surface water.

19 Claims, 1 Drawing Sheet

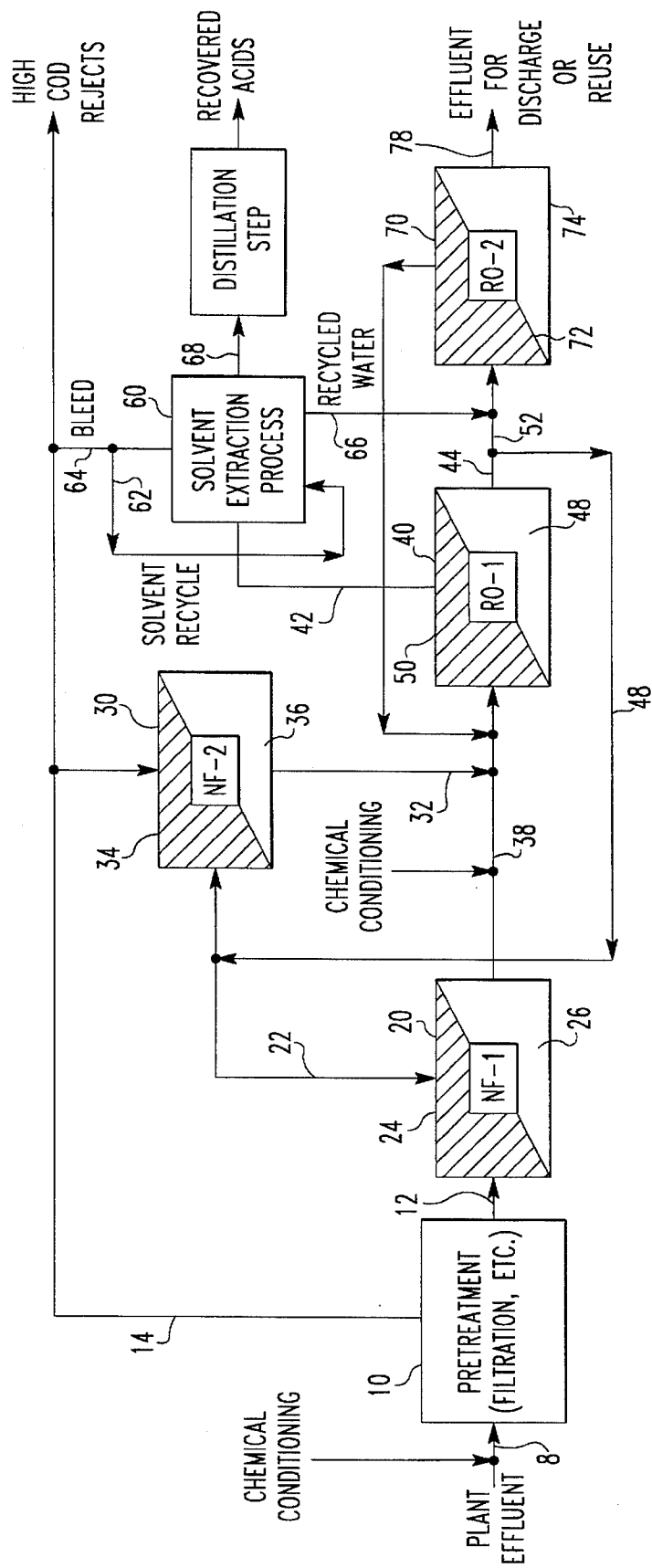

RECOVERY OF CARBOXYLIC ACIDS FROM CHEMICAL PLANT EFFLUENTS

INTRODUCTION

This invention relates to waste effluent streams containing low concentrations of carboxylic acids such as acetic acid or formic acid and more particularly, it relates to recovery of acetic acid or formic acid from aqueous effluent streams. The process of the invention also generates an environmentally compatible effluent which can be discharged or reused.

Aqueous streams from furfural plants, pulp digestion and the like contain relatively low concentrations of acetic acid and/or formic acid. Nevertheless, such dilute streams are environmentally unacceptable in view of their high chemical oxygen demand (COD) and environmental laws that prohibit their direct discharge into receiving waters. Many processes have been suggested to extract these acids from the aqueous stream. For example, direct extraction of the acids using packed column extractors and distillation columns have been used. However, generally this process is not favorable because of the high capital costs associated with the large equipment and the high operating costs of conventional extraction and distillation equipment. Such equipment can include a Karr column for solvent extraction followed by use of a dehydration column to remove water. Thereafter, the acids are stripped leaving behind high boiling solvents. Finally, the acids are distilled to purify the acetic or formic acids.

Other processes for purifying streams are set forth in the following patents.

U.S. Pat. No. 4,000,065 discloses a process for purifying aqueous streams contaminated with organic materials wherein aqueous streams contaminated with minor amounts of organic material are separated into two fractions. The contaminated aqueous stream is circulated from the high pressure compartment of a reverse osmosis unit to the high pressure compartment of an ultrafiltration unit, then to the low pressure compartment of the ultrafiltration unit, and then back to the high pressure compartment of the reverse osmosis unit. The contaminants are concentrated in the high pressure compartment of the reverse osmosis unit, and a portion thereof is precipitated or otherwise rendered amenable to removal along with ultra filtration concentrate.

U.S. Pat. No. 4,584,057 discloses that an aliphatic organic acid fraction is separated from kraft black liquor by subjecting the liquor to ultrafiltration, treating the resulting permeate by electrodialysis, acidifying the resultant deionate to about pH 4–5, separating the lignin solids which precipitate following this acidification, raising the pH of the separated solution to about 7–8 and finally subjecting the neutralized solution to electrodialytic water-splitting.

U.S. Pat. No. 4,655,928 discloses membrane processes for metal recovery and pollution control in metal process industries. The treatment of an aqueous stream containing an acid or base and typically a precipitatable material such as a metal ion comprises: (a) subjecting the aqueous stream to (i) a treatment to produce a relatively pure stream of water and a concentrated aqueous stream, and (ii) water splitting to produce a stream of base, a stream of acid and a dilute aqueous stream of a concentration lower than the concentrated aqueous stream, the treatments (i) and (ii) being effected in either order, and (b) recycling at least part of the pure water stream produced in (a)(i) to an earlier stream either in the production leading to said aqueous stream or to step (i) or (ii).

U.S. Pat. No. 4,728,393 discloses a method for obtaining deicers comprising using a black liquor obtained from a pulp mill operation, fractionating said black liquor into a low molecular weight fraction, and concentrating said collected low molecular weight fraction to produce a concentrated deicing product.

U.S. Pat. No. 4,808,287 discloses a water purification process wherein potable water from a municipal water supply is treated to remove suspended solids, organic and inorganic dissolved solids, dissolved carbon dioxide gas and metal contaminants so as to produce ultra-pure water in the 16 megohm-$cm^3$ and greater range. The process involves prefiltration of the water; activated carbon filtration; secondary guard filtration; double reverse osmosis treatment of the water. The process further involves the use of either an anion exchange or electrodialysis unit to remove further impurities from the water. A method for recycling part of the discharged water is also provided.

U.S. Pat. No. 4,250,182 discloses a membrane-based process for the recovery of lactic acid and glycerol from a corn thin stillage stream. In a first step, an ultrafiltration (UF) membrane means produces a UF permeate stream in which not only essentially all the insoluble portion of said thin stillage >0.05 μm is removed as UF concentrate, but also at least 50% of solubles having a molecular weight >$2 \times 10^5$ Daltons, including dissolved proteins in said thin stillage. In a second step to which the UF permeate is fed, a nanofiltration (NF) membrane produces an NF permeate with a rejection of less than 30% of both the lactic acid and the glycerol, preferably less than 25%. Essentially all molecules larger than lactic acid or glycerol are removed in the NF concentrate. In a third step, to which the NF permeate is fed, a reverse osmosis (RO) membrane means produces demineralized RO water which contains essentially no lactic acid and glycerol, because these are rejected in the RO concentrate. Use of the membrane separation process in the production of ethanol based on the dry-milling of corn, eliminates the use of a conventional evaporator.

U.S. Pat. No. 4,904,389 discloses a process for separation of multicomponent mixtures of dicarboxylic acids, especially, mixtures of $C_8$–$C_{24}$ saturated and unsaturated acids derived from a fermentation process in which an aqueous feed solution containing the mixture of dicarboxylic acids is adjusted in pH value depending on the permeability of the component to be separated. Over 95% of the saturated component is separated from the unsaturated material by passing the mixture through a membrane filter.

U.S. Pat. No. 5,145,584 discloses processes for using a thin film ultrafiltration membrane for the separation of low molecular weight solutes such as the separation of glucose from sucrose and higher molecular weight sugars and the separation of amino acids from oligopeptides and polypeptides. The membrane possesses desirable properties or characteristics, and may be prepared by casting a solution of a polyelectrolyte complex on a microporous support to form a thin film of polyelectrolyte complex on the surface of the support. The thickness of the membrane will range from about 600 to 3,000 Å.

U.S. Pat. No. 5,248,427 discloses a process for removing water by pervaporation or vapor permeation from mixtures with alcohols and/or carboxylic acids and/or carboxylic esters by bringing the mixture into contact with one side of a membrane and removing the water-containing permeate in vapor form from the other side of the membrane, the membrane used has been obtained by plasma polymerization.

U.S. Pat. No. 5,167,826 discloses an apparatus and a process for recycling used engine coolant employing a reverse osmosis process for separating ethylene glycol from a concentrate coolant solution. The engine coolant concentrate is pre-filtered through a series of filters and pressurized prior to being passed through a semi-permeable membrane. The membrane separates the feed stream into a permeate solution of ethylene glycol and water and concentrate solution. The concentrate solution is returned to a concentrate tank for continuous circulation through the apparatus. A heat exchanger maintains the temperature of the concentrate solution below a pre-established threshold.

Thus, it will be seen that there is a great need for an economically viable process that efficiently extracts the carboxylic acids from dilute aqueous effluent streams.

SUMMARY OF THE INVENTION

It is an object of this invention to recover carboxylic acids from aqueous waste streams.

It is another object of this invention to recover acetic and/or formic acid from aqueous waste streams.

Yet, it is another object of this invention to provide a process utilizing reverse osmosis to recover carboxylic acids from aqueous waste streams.

And yet, it is a further object of this invention to provide a process comprising pretreatment (e.g., chemical conditioning, settling, prefiltration), membrane separation and solvent extraction to recover carboxylic acids from waste streams and produce clean effluent.

These and other objects will be apparent from reading the specification and claims and an inspection of the FIGURE appended hereto.

In accordance with these objects, there is provided a method of removing carboxylic acids from effluent streams comprising the steps of chemical conditioning and/or filtering the effluent stream to remove suspended solid particles to provide a filtered stream and subjecting the filtered stream to membrane filtration in the nanofiltration range to separate organic compounds having a molecular weight of greater than approximately 150 while simultaneously permitting permeation of the membrane by the carboxylic acids to provide a membrane filtered stream containing purified acids. A single-pass or double-pass reverse osmosis membrane is provided having a high pressure side and a low pressure side, and the membrane filtered stream is introduced to the high pressure side of the reverse osmosis membrane. The carboxylic acids are concentrated in the high pressure side of the reverse osmosis membrane, and purified liquid is passed to the low pressure side of the reverse osmosis membrane for ultimate reuse or discharge. The concentrated acids are then sent to acid extraction systems using high-boiling or low boiling solvents in order to recover the acids.

BRIEF DESCRIPTION OF THE FIGURE

The FIGURE is a schematic illustrating steps in recovery of carboxylic acids from organically contaminated or inorganically contaminated aqueous effluent streams.

DETAILED DESCRIPTION OF PREFERRED EMBODIMENTS

The process in accordance with the present invention overcomes the technical and economic problems of existing technology by providing novel technology that is efficient and cost effective for purification and concentration of dilute streams containing relatively low concentrations of carboxylic acids. Pretreatment, prepurification and concentration of the acids in the dilute stream permits efficient solvent extraction and acid dehydration. Briefly, the new process employs a solids separation step that may utilize microfiltration, ultrafiltration, cyclonic separation, gas flotation, chemical flocculation, settling, sand bed and/or cartridge filters as a pretreatment step. Further, the process purifies carboxylic acids by membrane (nano)filtration. That is, the membrane filtration removes the bulk of organic contaminants having a molecular weight of about 150 or greater, for example, from the pretreated aqueous effluent stream while permitting the bulk of carboxylic acids to pass through the membrane in the permeate stream. Thereafter, the permeate stream is introduced to the high pressure side of a single-pass or a double-pass reverse osmosis membrane where the carboxylic acids are concentrated and a purified aqueous stream substantially free of carboxylic acids and other organic and inorganic contaminants is removed from the low pressure side as permeate suitable for discharge or reuse. The concentrated carboxylic acids in the retentate now can be efficiently and economically recovered by solvent extraction or other separation means.

Referring now to the FIGURE, there is shown a schematic of a process in accordance with the invention to recover carboxylic acids from aqueous waste streams such as would be encountered from a furfural production plant. Thus, generally, in first step 10, plant effluent is first pretreated or filtered to separate and remove suspended solids before being passed along line 12 to the membrane prepurification step, step 20, also called the nanofiltration step which removes heavy organic compounds such as sugars, furfural polymerization products, high molecular weight carboxylic acids, etc. High molecular weight contaminants removed in filtration step 20 may be removed along line 14 to an incinerator. Preferably, the majority of heavy organic compounds are removed by membrane filtration while permitting the majority of carboxylic acids to permeate through the nanofiltration membrane (NF-1) and be carried along line 38 to reverse osmosis separation steps 40 and 70. The heavy organic compounds (other than carboxylic acids) can be removed in one or more steps. In the embodiment shown in the FIGURE, retentate from first step 20 (i.e., NF-1) is shown being removed along line 22 to a second NF membrane filtration step 30 (i.e., NF-2). In addition to further volume reduction and concentration of heavy organic contaminants in the retentate, the second NF membrane stage will allow further recovery of the small amount of carboxylic acids rejected by the first membrane purification step (NF-1). However, in certain cases, a single membrane separation step 20 may be employed. Further, concentrate of heavy organics, sugars, etc., from membrane filtration step 30 may be introduced to line 14 and carried to an incinerator or other means for removing such materials from the system. Permeate from membrane filtration step 30 (i.e., NF-2) can be removed along line 32 and introduced to line 38 for separation of carboxylic acids contained therein in reverse osmosis separation steps 40 (i.e., RO-1) and/or 70 (i.e., RO-2). Retentate from the reverse osmosis separation step 40 (i.e., RO-1) is removed along line 42 to solvent extraction or other acid recovery means, step 60. Permeate or clean effluent from reverse osmosis separation step 40 is removed along line 44 for disposal or, in a preferred embodiment, the first pass RO-1 permeate is sent for processing using a second pass reverse osmosis membrane step 70 (i.e., RO-2) in order to produce "high purity treated water" for further in-plant use. In another preferred embodiment, the first pass RO-1 permeate removed along line 44 is neutralized with lime, magnesium hydroxide or caustic soda before final treatment with the second pass reverse osmosis membrane (RO-2) in order to maximize the separation of metal acetate and formate in their ionized form and produce a high purity "low COD" treated water that can be used as boiler feed water, thus saving material and energy costs and further enhancing the economic merits of this process.

In another preferred embodiment, a recycle stream 46 is returned for introduction to second nanofiltration separation step 30 as explained in detail later. Further, in addition to the recovery of "high purity" acetic acid from the acid recovery step 60 via line 68, water from the extraction process, contaminated with acids, is recycled via line 66 for further treatment using the second pass reverse osmosis step 70 (i.e., RO-2) in order to maximize water recovery (approximately 95% recovery).

1. Pretreatment Step 10

Plant effluent being introduced by the process of the invention along line 8 can contain up to 0.2 wt. % suspended solids and more typically 0.1 wt. % solids. Such solids typically are comprised mainly of insoluble organic polymers of furfural and its derivatives, cellulose fibers, dust and other inorganic airborne contaminants. These suspended solids must be removed efficiently in order to prevent fouling of membranes such as narrow-spaced spiral-wound membranes used downstream. Deposition under pressure of the said suspended solids on the surfaces of these membranes will result in "blinding" of the surface and loss of separation effectiveness (i.e., rejection), permeate flux and throughput.

Thus, typically less than 20 mg/L solids and preferably less than 5 mg/L solids remain in stream 12, and such solids typically have a particle size of less than 1 μm. Further, pretreatment or filtration 10 should be selected to permit high recovery of solution being forwarded along line 12 to separation step 20. Thus, recovery should be at least 90% and preferably greater than 98% and typically in the range of 98 to 99%. As noted, the solids filtered out in step 10 are removed along line 14 to be disposed of, for example, by incineration in the plant's boiler furnaces or by other suitable means. If desirable, the solids may be further dewatered before being removed and the water introduced to line 12 to recover carboxylic acids contained therein.

Typically, the plant effluent can contain carboxylic acids such as acetic acid, formic acid, and smaller concentrations of "contaminants" such as higher molecular weight acids, furfural, hydroxymethyl furfural, sugars and other furfural and organic by-products. The amount of carboxylic acids is usually dilute, for example, up to 1 or 2 wt. %.

The types of separation means used to remove suspended solids include ultrafiltration, microfiltration, sand bed or multi-media filters, cartridge filters and the like. Ultrafiltration uses polymeric or ceramic membranes to separate all suspended solids and high molecular weight polymers possessing a size range of 0.005 μm to 0.1 μm.

Microfiltration uses polymeric or ceramic membranes or porous sintered metal filters to separate all suspended solid particles of a typical size range of 0.1 μm to 10 μm and more typically in the size range 0.1 to 2 μm.

Sand bed and multi-media filters are self descriptive and remove particles down to a size range of 20 μm to 50 μm. Cartridge filters are also suitable as polishing filters and may be selected to remove particles down to a size of 0.05 μm.

Although tubular or hollow fiber micro filtration membranes (MF) offer the most effective "technical" means to separate all suspended matter down to a size of 0.1 μm, these membranes are costly, especially when applied to large effluent streams in the range 100 gpm to 2000 gpm and more, typically 500 gpm to 1000 gpm as in the case of furfural plant effluents. In addition to the MF membrane system cost, these systems also incur substantial operating costs associated with pumping power, the use of chemicals to periodically clean the membranes and the cost of replacement of membranes once they become irreversibly fouled and lose productivity. Ultrafiltration membranes (UF) also offer a good "technical solution" to the problem of separating suspended solids. However, these "tighter" membranes are even more costly than MF membranes and incur higher operating costs in view of their lower permeate flux (i.e., permeate flowrate per unit area of membrane surface per unit time) and higher operating pressure, respectively. Porous sintered stainless steel filter may also be effective in separating the solids down to approximately 1 μm size. However, these are extremely costly when compared to polymeric or ceramic membranes. While any of the above-mentioned filtration methods will provide suitable pretreatment before the spiral-wound nanofiltration step 20, the preferred approach is to use a combination of chemical conditioning (i.e., chemical coagulants and flocculants) followed simply by gravity settling or other more efficient means to clarify the liquid such as inclined plate clarifiers, and then followed by filtration of the supernatant (i.e., clarified liquor) through a back-washable sand or multi-media bed and followed by a final polishing step involving the use of "tight" depth-type or membrane-type "dead-end" cartridge filters. These filters will have an absolute particle separation in the range of 0.1 μm to 2 μm and preferably 0.5 μm to 1 μm. As polishing filters, these cartridge filters will separate relatively small solid loadings since the bulk of the solids will have been removed by coagulation, flocculation, settling and sand bed or multi-media filtration. The cartridge filters can be backwashed at low pressure, but eventually they will be loaded up with solids and must be disposed of and replaced. The above-described pretreatment scheme is the least costly method, especially for large effluent streams. Other advantages include the relatively low operating costs (i.e., low pressure pumping, low ppm flocculant and cartridge filter replacement) and the high water recovery achievable in this "dead-end" filtration mode. A water recovery in the range of 98–99% can be attainable using this pretreatment method.

The filtered aqueous stream is passed along line 12 to separation step 20. However, preferably a chemical conditioner is added prior to the stream being introduced to separation 20.

2. Nanofiltration Step 20

This solids-free effluent from the pretreatment step 10 (i.e., stream 12) is introduced to high pressure side 24 of a nanofiltration membrane separation unit 20. The membrane in unit 20, which is preferably the spiral-wound type, is selected to permit the passage of low molecular weight carboxylic acids therethrough (especially acetic, formic, etc.) and to reject other higher molecular weight organic compounds such as sugars and organic acids and other organic compounds typically having molecular weights in excess of 150. In this manner, the permeated acids will contain only a small concentration of contaminants thereby minimizing the fouling potential in the RO membrane and improving the efficiency of the acid extraction and/or recovery process downstream. By removing most of these contaminants upstream, the acid recovery process can be simplified in terms of extent, size of equipment and fouling of surfaces. This will also enable production of purer acids in a more cost-effective manner. As indicated above, separation of high molecular weight organic contaminants and sugars in the nanofiltration step 20, in addition to providing a purer feed to the RO and finally to the solvent extraction and/or acid recovery step 60 will also result in minimum fouling of the RO membrane surface since these compounds will concentrate up to 10 times their original concentration and will likely become insoluble and deposit on the RO membrane surface. Deposition on the NF membrane surface is prevented by operating the NF membrane at a relatively high temperature of 40°–50° C. and preferably 41°–42° C. Permeate containing carboxylic acids is collected on low pressure side 26 after passing through nanofiltration membrane in step 20.

In subjecting filtered aqueous stream 12 to nanofiltration separation step 20, a certain amount of liquid containing residual sugars, hemicellulose and high molecular weight acids and derivatives of furfural is removed along line 22. Such liquid can contain carboxylic acids. It represents a loss of liquid flow through the system and can be in excess of 5%, for example, 10% of the influent volume. This can represent an up to 10% loss of recovery of carboxylic acids or water in the system, and thus, it is preferred to minimize such loss. Thus, preferably, water recovery in nanofiltration step 20 is maintained at 90% or greater and preferably 95% or greater. This high water recovery can be achieved at a relatively low cost by using spiral-wound nanofiltration membranes containing a high membrane surface area per unit volume. Typical nanofiltration membranes are available from Desalination Systems Inc. of California under the trade name DS-5-DK8040. The use of these membranes is made possible by providing adequate pretreatment to separate suspended solids efficiently, as described earlier. The NF membrane can be operated in the pressure range 100 to 450 psig, and more preferably at 300 psig on the high pressure side 24, in order to minimize the pumping power consumption as well as to reduce the potential of fouling of the NF membrane surface.

3. Second Nanofiltration Step 30

To further concentrate sugars, organic acids, etc., having average molecular weights greater than 150 and to recover low molecular weight carboxylic acids (viz., acetic acid and formic acid), concentrate stream 22 leaving nanofiltration separation step 20 (i.e., NF-1) may be subjected to a further or second nanofiltration separation step 30. Thus, concentrate stream 22 is introduced to high pressure side 34 of nanofiltration unit 30. Because the concentration of sugars and organic compounds having an average molecular weight greater than 150 can be sufficiently high to provide a significant osmotic pressure and precipitate on the membrane in nanofiltration unit 30, a diluent stream 46 which may be equal in volume to NF-1 retentate stream 22, may be recycled from the "low carboxylic acid" permeate line 44 leaving reverse osmosis unit 40 (RO-1 ). Because the permeate leaving reverse osmosis unit 40 is relatively pure and free of heavy organic contaminants, its introduction to line 22 or high pressure side 34 of unit 30 permits further removal of carboxylic acids contained in the concentrate from the first nanofiltration step by permeation through the second nanofiltration membrane (NF-2) at an operating pressure in the range 200–450 psig and more preferably at 250 psig. Thus, introduction of stream 46 to stream 22 permits not only further recovery of carboxylic acids but it also aids in avoiding precipitation of high molecular weight organic compounds on the membrane in second nanofiltration step 30. Preferably, at least 90% of liquid introduced to high pressure side 34 is recovered as permeate in low pressure side 36. The recovery of carboxylic acids is increased from approximately 92% using a single nanofiltration membrane step to approximately 98% using the second stage NF membrane (NF-2) described herein. Thus, approximately 98% of the carboxylic acids in the plant effluent is introduced to reverse osmosis unit 40. The second nanofiltration step will also provide the important advantage of reducing the volume of stream 22 which contains the concentrated organic contaminants by approximately 80%. In fact, because of the recycle maintained between low pressure side 48 of reverse osmosis unit 40 and second nanofiltration unit 30, the flow rate along line 38 to high pressure side 50 can be higher than flow rate of plant effluent 8. However, it will be noted that recycle 46 aids in making the present invention exceptionally efficient in removing carboxylic acids from plant effluent.

4. First Pass Reverse Osmosis Step 40

Plant effluent which has been filtered and from which undesirable organic compounds have been removed but which contains said carboxylic acids is combined with the system's second pass (RO-2) membrane retentate and then introduced to high pressure side 50 of reverse osmosis separation unit 40 (RO-1), operated at 500–1000 psig, and more typically at 800–900 psig, for the separation and concentration of carboxylic acids contained in said stream 38. An antifoulant "conditioning chemical" may be added to stream 38 in order to minimize the potential for deposition of trace amounts of high molecular weight organic compounds on the membrane surface and prevent fouling. These conditioning chemicals have proprietary chemical formulae but are typically organic, polymeric compounds with a number of functional groups that increase the solubility of such insoluble heavy organic contaminants and increase the hydrophilic nature of the membrane surface, thereby enhancing the permeation of water. Operation at slightly elevated temperatures (i.e., 35°–40° C.) will usually improve solubility of organic compounds and alleviate fouling of the membrane surface. However, it is preferred to operate the RO membranes at the lower temperature range of 20°–30° C. and preferably 25°–30° C. in order to maximize the separation efficiency of the recovered carboxylic acids (e.g., acetic acid and formic acid). The carboxylic acids can be concentrated up to 8 wt. % or higher and typically up to 10 wt. % in high pressure side 50 in the reverse osmosis retentate. Reverse osmosis membranes suitable for such separation are available from Filmtec Corporation under the trade name FT30SW-HR 8040. As noted, purified water is removed from low pressure side 48 and a portion in the range 5–10% by volume is recycled to the second stage nanofiltration unit 30 (i.e., NF-2).

For purposes of removing and recovering pure, concentrated carboxylic acids from concentrate stream 42 leaving reverse osmosis step 40, solvent extraction, dehydration or distillation or a combination of these processes may be used. In the method of separating carboxylic acids from the water in the concentrate or retentate from the high pressure side of the reverse osmosis membrane, it is preferred to subject the relentate to liquid-liquid or solvent extraction to remove the carboxylic acids from the water. The liquid-liquid extraction is highly suitable to remove low concentrations of carboxylic acids, e.g., 4 to about 10 wt. % or higher, where subsequently the carboxylic acids are distilled off leaving the solvent for reuse. That is, it is more efficient to extract the low amount of carboxylic acids from the water with a solvent than to distill the water off. Any extraction solvent that is efficient in extracting the carboxylic acids from the liquid phase in a column may be used. However, an extraction solvent should be selected so as to provide different boiling points from the carboxylic acids and permit ease of subsequent separation later. The extraction solvent can be a low or high boiling point solvent.

After liquid-liquid extraction, the extraction solvent containing carboxylic acids may be subjected to a dehydration step to remove residual water that was extracted with the carboxylic acids in the extraction solvent. Thus, the water may be removed in a dehydration column leaving extraction solvent and carboxylic acids. The extraction solvent and carboxylic acid is then subjected to a distillation step to remove carboxylic acids from the extraction solvent. The extraction solvent may be recycled to the liquid-liquid extraction column for reuse in further removing carboxylic acids. It will be appreciated that liquid-liquid extraction, dehydration and distillation can be connected for efficient movement of the different liquids. Also, it will be understood that other processes may be used for removing the carboxylic acids in reverse osmosis retentate stream 42 from the water and such is contemplated within the invention.

The reverse osmosis step is limited in concentration of the carboxylic acids, e.g., acetic acid, because of the high osmotic pressure of acetic acid. The osmotic pressure of acetic acid is about 4.4 atmos./wt. % of acetic acid in the reverse osmosis retentate. Thus, at about 10% concentration, the osmotic pressure is about 44 atmospheres. About 80% of the carboxylic acids in the feed to the high pressure side of the reverse osmosis unit can be separated. For further acid recovery and in order to further purify the water (viz., RO-1 permeate) for the purpose of plant reuse, a second reverse osmosis step can be employed and the concentrate therefrom recycled back to the RO-1 feed line (line 38) in order to maximize the acid recovery, as shown in the FIGURE.

The carboxylic acids concentrate is removed along line 42 for treatment to further concentrate, purify and recover the carboxylic acids (e.g., acetic and formic). In step 60, for example, the carboxylic acids can be separated from the water. Any efficient separation system may be used for this step of the process.

The recovered pure carboxylic acids from the final acid recovery process will be sold as useful products and water therefrom may be discharged or reused after further purification in a second pass reverse osmosis unit 70 (RO-2). As shown in the FIGURE, the solvent is recovered by stripping off the acids and is recycled along line 62 to the solvent extraction column. A small solvent bleed stream is removed along line 64 and disposed of via incineration along line 14, or other disposal means in order to prevent build-up of contaminants in the solvent. The water (e.g., raffinate) from the solvent extraction column will typically contain 0.1–0.2 wt. % of carboxylic acids which represents up to 2% of the total acid value in the plant effluent. This represents a significant quantity of acid which can be subjected to further recovery by using a second pass reverse osmosis unit 70, as shown in the FIGURE.

5. Second Pass Reverse Osmosis Unit Step 70

Aqueous permeate from the first reverse osmosis unit 40 containing approximately 0.25 wt. % carboxylic acids and traces of other low molecular contaminants is admitted via line 52 into the high pressure side 72 of the second reverse osmosis step, unit 70. The objectives of this step are: (a) to increase carboxylic acid recovery from approximately 80% to approximately 95% which adds to the economic merits of the process; (b) to further recover acid from the dilute aqueous raffinate from the solvent extraction unit 60 (i.e., from recycled water stream 66); and (c) to further purify water obtained from the first reverse osmosis step by separating most of the remaining carboxylic acids and other organic contaminants and producing water than can be reused either as process water for cooling, etc., or as a boiler feedwater, after heat exchange with incoming hot plant effluent. In this manner, approximately 95% of clean and hardness-free water and approximately 50–60% of the energy associated with the hot plant effluent is recovered simultaneously. The recycle and reuse of water also results in savings in operating costs of the water treatment plant (i.e., savings in power, chemicals and labor).

Therefore, the carboxylic acids in RO-1 permeate stream 52 are concentrated from approximately 0.25 wt. % to approximately 2.4 wt. % in the RO-2 retentate stream 76. The high pressure side 72 of the second reverse osmosis system (unit 70) is operated at a pressure in the range 500–1000 psig and preferably in the range 800–900 psig. At least 90% of the water is recovered from the low pressure side 74 of this RO unit with a preferred recovery being in the range 92–95%, depending on the quality criteria of the treated second pass RO-2 permeate that would be required for reuse of the water (i.e., concentration of residual acids, chemical oxygen demand, COD, concentration of metals and anions, etc.). The higher the water recovery, the "poorer" the treated water quality. As can be seen from examination of the FIGURE, the second reverse osmosis step, unit 70, can reduce the concentration of carboxylic acids in the effluent from approximately 0.25% to approximately 0.06% or 600 mg/L, based on a typical RO membrane rejection of carboxylic acids of approximately 90%. The rejection is defined as the concentration of acids in the retentate or concentrate minus the concentration in the permeate, divided by the concentration in the retentate, i.e., $R=(C_c-C_p)/C_c$.

Reverse osmosis membranes suitable for such separation are available from Filmtec Corporation under the trade name FT30SW-HR 8040. As noted, purified water is removed from low pressure side 74 via stream 78 and is discharged or reused by the plant.

In a preferred embodiment, the permeate from the first reverse osmosis step (line 52), containing approximately 0.25% carboxylic acids, is first neutralized by adding a suitable neutralizing agent such as calcium hydroxide lime or magnesium hydroxide or caustic soda, thereby raising the pH from approximately 2.7 to a pH in the neutral range 5.5–9.5 and preferably 6–6.5. The carboxylic acids are thus converted to their ionized salts (e.g., calcium acetate and calcium formate) which are rejected much more efficiently by the second pass RO membrane (unit 70). Typically, the rejection of these ionized salts of the said carboxylic acids by the said membrane will be increased from 90% to approximately 99%, thus bringing about an order of magnitude improvement in the second pass RO membrane permeate quality. In the case of this preferred embodiment, the RO-2 permeate which is removed via line 78 will contain only about 60 mg/L of carboxylic acids, one order of magnitude lower than the 600 mg/L obtained in the absence of acid neutralization. Since this second pass RO-2 permeate will be almost entirely free of hardness and will also have very low electrical conductivity and chemical oxygen demand (viz.,<100 µS/cm and <100 mg/L COD, respectively), it will be possible to use this water as boiler feedwater, after polishing through an ion exchange column. In this manner, a great deal of savings will be realized in terms of material (i.e., water treatment chemicals) and energy (via heat exchange with hot incoming plant effluent). The retentate from the second reverse osmosis step 70 of this preferred embodiment will contain approximately 4% of the calcium or other metal salt of carboxylic acids, based on a water recovery of approximately 92%. Further water recovery (e.g., up to approximately 95%) from unit 70 is possible, thus reducing the volume of the retentate from RO-2 from approximately 8% to approximately 5% of the incoming plant effluent (line 8). The salt concentration of retentate at 95% recovery will be approximately 6%. The salt can be recovered, possibly as road deicing salt, by using an evaporator, crystallizer or spray dryer.

The present invention is advantageous in that it removes materials that would interfere with the carboxylic acids extraction and/or recovery process. Further, such purification permits more efficient operation of the reverse osmosis membrane used to preconcentrate the acids. Another advantage of the process is the dramatic reduction in the amount of water required to be treated in the carboxylic acids recovery step. That is, water to be treated is reduced by a factor of about 10. Thus, solvent extraction, dehydration and/or distillation equipment can be more efficiently used to recover the carboxylic acids from the waste effluent stream. In addition, capital and operating costs of the process are reduced providing a short payback period on the order of 3 to 5 years. Further, while a single pass reverse osmosis process produces good quality final effluent that can be discharged to sanitary sewers, a double pass reverse osmosis membrane incorporating pH adjustment will produce good quality final effluent that can be discharged to surface water or reused for cooling or as boiler feedwater after final polishing with ion exchange.

The following example is still further illustrative of the invention.

EXAMPLE

Aqueous plant effluent containing approximately 10,000 ppm carboxylic acids (acetic acid 0.95% and formic acid 0.05%) is pumped to a pretreatment unit involving the addition of 4 ppm of a coagulant and 2 ppm of a flocculant, settling of the floc, decanting of the supernatant and pumping it through a graded sand-bed filter containing coarse sand and fine sand followed by a 1 µm absolute cartridge filter at a rate of about 1000 gpm (gallons/minute) at approximately 40° C. and at a pH of 2.8 to remove the suspended solids therefrom. From the filtration treatment, a reject stream will be removed at about 20 gpm and containing about 5 wt. % solids. Filtered effluent is removed at a rate of 980 gpm.

The filtered effluent is added to the high pressure side of a first nanofiltration filter to separate sugars and organic compounds (other than carboxylic acids) having an average molecular weight greater than about 150 as well as any inorganic "hardness-causing" compounds from the filtered effluent. Permeate containing carboxylic acids from the first nanofiltration unit is removed at about 931 gpm and a concentrate containing sugars and organic compounds (MW>150) is removed from the high pressure side at a rate of about 49 gpm. The concentrate from the first nanofiltration unit is then diluted with low-acid water recycled at an equal rate of 49 gpm from the first pass reverse osmosis unit to provide a flow rate of about 98 gpm to a second nanofiltration unit. The second nanofiltration unit further reduces the volume and concentrates the high MW organics, etc., as rejects and permits separation of water therefrom containing carboxylic acids. The rejects are removed from the second nanofiltration step in a stream at about 9.8 gpm and the carboxylic acid containing permeate stream is removed at about 88.2 gpm.

The 9.8 gpm NF-2 reject stream is added to the 20 gpm solids-containing stream from the pretreatment step and incinerated. The 88.2 gpm permeate stream from the second nanofiltration stream is added to the carboxylic acids-containing permeate stream from the first nanofiltration unit and both comprising a rate of about 1019.2 gpm and containing approximately 0.96% carboxylic acids are combined with 79.1 gpm of recycled RO-2 retentate and added to the high pressure side of a first pass reverse osmosis membrane separation unit to remove and concentrate the carboxylic acids contained in the water. Permeate containing approximately 2500 ppm carboxylic acids from the first reverse osmosis unit is removed at a rate of 988.5 gpm. The first pass reverse osmosis retentate of about 109.8 gpm and containing preconcentrated carboxylic acids (approximately 8.4 wt. %) is removed from the high pressure side of the reverse osmosis unit and forwarded to an acid recovery unit (e.g., a solvent extraction unit). The carboxylic acids are separated from the water stream at a rate of about 8.6 gpm of pure acetic acid and formic acid using the solvent extraction unit. Water containing approximately 1800 ppm of acids is removed from the solvent extraction unit at about 100.8 gpm and it is combined with the first RO permeate producing about 1040.3 gpm of water containing about 2400 ppm of carboxylic acids which is introduced into the high pressure side of a second reverse osmosis unit. The second RO unit separates most of the remaining acids and produces a retentate of about 79.1 gpm and containing about 2.4% acids which is recycled to the first RO step for further acid recovery. Permeate from the second pass RO will contain only about 600 ppm of carboxylic acids, corresponding to an overall process acid recovery of about 91% and overall process water recovery of about 96%. This final effluent can be discharged to sanitary sewers or surface water or it can be recycled as process water after neutralization. In a second example, the combined water stream from RO-1 and the solvent extraction unit is first neutralized with a higher pH neutralizing agent (e.g., calcium hydroxide) and then treated with the second pass RO unit, yielding a treated permeate containing only about 60 ppm of neutralized acid salts. This high quality water can be used as a boiler feedwater after polishing with an ion exchange unit to remove trace ions. The total effluent flow rate for incineration purposes is about 30 gpm, containing about 1.1% acids, including a small bleed stream of 0.2–0.5 gpm from the solvent extraction unit used to control the build-up of heavy organics in the recovered solvent.

Thus, it will be seen that instead of subjecting 1000 gpm of plant effluent to solvent extraction which is very costly, only about 110 gpm was introduced to the solvent extraction unit, greatly reducing the cost of recovering carboxylic acids from the plant effluent.

While the invention has been described in terms of preferred embodiments, the claims appended hereto are intended to encompass other embodiments which fall within the spirit of the invention.

What is claimed is:

1. A method of removing low concentrations of carboxylic acids from aqueous effluent streams comprising the steps of:

(a) filtering said effluent stream to remove solid particles to provide a filtered stream; and (b) introducing said filtered stream to the high pressure side of a first nanofiltration membrane to concentrate organic compounds having an average molecular weight of greater than 150 in the high pressure side to provide a first organic concentrate stream while simultaneously permitting permeation of said membrane by said carboxylic acids to provide a first nanofiltration membrane permeate stream containing carboxylic acids; thereafter (c) introducing said first organic concentrate stream to a high pressure side of a second nanofiltration membrane to provide a second organic concentrate stream containing organic compounds having a molecular weight of more than 150 while simultaneously permitting permeating of said second nanofiltration membrane by said carboxylic acid to provide a second nanofiltration membrane permeate stream containing carboxylic acids;

(d) providing a first reverse osmosis membrane having a high pressure side and a low pressure side;

(e) introducing said first and second nanofiltration membrane permeate streams to the high pressure side of said first reverse osmosis membrane;

(f) concentrating said carboxylic acids in the high pressure side of said reverse osmosis membrane to provide a concentrated carboxylic acids retentate and passing a purified aqueous stream to the low pressure side of said reverse osmosis membrane to provide a purified aqueous stream;

(g) recirculating a portion of said purified aqueous stream from the low pressure side of said first reverse osmosis membrane to the high pressure side of said second nanofiltration membrane; and (h) treating said concentrated carboxylic acids retentate to recover carboxylic acids therefrom.

2. The method in accordance with claim 1 wherein the acids are selected from the group consisting of acetic acid and formic acid.

3. The method in accordance with claim 1 wherein in said filtering step, particles having a size greater than 1 micron are removed.

4. The method in accordance with claim 1 including extracting carboxylic acids from said concentrated carboxylic acids retentate.

5. The method in accordance with claim 4 including using a solvent to extract said carboxylic acids from said concentrated carboxylic acids retentate to provide a solvent and carboxylic acids stream and water stream containing not more than 2000 ppm carboxylic acids.

6. The method in accordance with claim 5 including dehydrating said solvent and carboxylic acids stream to remove residual water therefrom that was extracted with the carboxylic acids to provide a solvent-carboxylic acids dehydrated stream.

7. The method in accordance with claim 6 including distilling said solventcarboxylic dehydrated stream to separate carboxylic acids from said solvent.

8. The method in accordance with claim 1 including recovering at least 90% of said carboxylic acids from said effluent aqueous stream.

9. The method in accordance with claim 1 including recovering at least 95% water having less than 100 ppm carboxylic acids from said effluent aqueous stream.

10. The method in accordance with claim 1 including providing a second reverse osmosis membrane having a high pressure side and a low pressure side and introducing purified aqueous stream to the high pressure side of said second reverse osmosis membrane from said low pressure side of said first reverse osmosis membrane to further concentrate carboxylic acids remaining in said purified aqueous stream and to provide a purified permeate aqueous stream from said second reverse osmosis membrane.

11. The method in accordance with claim 10 including introducing said water stream containing not more than 2000 ppm carboxylic acids from said solvent extraction step to the high pressure side of said second reverse osmosis membrane.

12. The method in accordance with claim 10 including adjusting the pH of said purified aqueous stream to a pH in the range of 5.5 to 9.5 prior to introducing to the high pressure side of said second reverse osmosis membrane.

13. The method in accordance with claim 10 wherein said purified permeate aqueous stream from said second reverse osmosis membrane has a COD of less than 1000 ppm.

14. The method in accordance with claim 1 including recirculating 5 to 10% of said purified aqueous stream from said first reverse osmosis membrane to the high pressure side of said second nanofiltration membrane.

15. The method in accordance with claim 1 including concentrating said carboxylic acids from less than 2 wt. % to at least 8 wt. % in said concentratd carboxylic acids retentate.

16. A method of removing organic acids including acetic acid and/or formic acid from an aqueous waste stream comprising the steps of:

(a) pretreating said aqueous waste stream to remove suspended solid particles therefrom to provide a substantially solid-free filtered stream;

(b) introducing said filtered stream to the high pressure side of a first nanofiltration membrane to concentrate organic compounds having an average molecular weight of greater than 150 in the high pressure side to provide an organic concentrate stream while simultaneously permitting permeation of said membrane by an organic acid selected from the group consisting of acetic and formic acid to provide a membrane filtered stream containing said organic acid;

(c) providing a first reverse osmosis membrane having a high pressure side and a low pressure side;

(d) introducing said membrane filtered stream to the high pressure side of said first reverse osmosis membrane;

(e) concentrating said organic acid in the high pressure side of said first reverse osmosis membrane to provide a concentrated aqueous retentate and passing a purified aqueous stream containing a residual of said organic acid to the low pressure side of said first reverse osmosis membrane to provide a recovered aqueous stream;

(f) adjusting the pH of said purified aqueous stream from said low pressure side of said first pass reverse osmosis membrane to a pH in the range of 5.5 to 9.5 to provide a neutralized aqueous stream;

(g) introducing said neutralized aqueous stream to a high pressure side of a second reverse osmosis membrane to provide a retentate stream and simultaneously therewith providing a high purity effluent permeate on a low pressure side of said second reverse osmosis membrane;

(h) introducing said organic concentrate stream from the high pressure side of said first nanofiltration membrane to a high pressure side of a second nanofiltration membrane to provide a second smaller organic concentrate stream of organic compounds having an average molecular weight greater than 150 and simultaneously therewith permitting permeation of said second nanofiltration membrane by said acetic acid or formic acid to provide a second nanofiltration membrane filtered stream;

(i) recirculating a portion of said purified aqueous stream from the low pressure side of said first reverse osmosis membrane to the high pressure side of said second nanofiltration membrane;

(j) adding said second nanofiltration membrane permeate stream to the high pressure side of said first reverse osmosis membrane; and (k) removing organic acids from said concentrated aqueous retentate of said first reverse osmosis membrane.

17. The method in accordance with claim 16 including using a solvent to extract said carboxylic acids from said concentrated aqueous retentate to provide a solvent and carboxylic acids stream and water stream containing not more than 2000 ppm carboxylic acids.

18. The method in accordance with claim 16 including dehydrating said solvent and carboxylic acids stream to remove residual water therefrom that was extracted with the carboxylic acids to provide a solvent-carboxylic acids dehydrated stream.

19. The method in accordance with claim 18 including distilling said solvent-carboxylic dehydrated stream to separate carboxylic acids from said solvent.

* * * * *